United States Patent [19]

Burton et al.

[11] Patent Number: 4,866,063

[45] Date of Patent: Sep. 12, 1989

[54] DIOL METABOLITES OF 7-PHENYL-1,2,4-TRIAZOLO[2,3-C]PYRIMIDINES-5-AMINES

[75] Inventors: Earl G. Burton, Deerfield; Christopher P. Chengelis, Chicago; Gerald M. Walsh, Lindenhurst, all of Ill.

[73] Assignee: G. D. Searle & Co., Chicago, Ill.

[21] Appl. No.: 289,068

[22] Filed: Dec. 22, 1988

[51] Int. Cl.$^4$ .................. A61K 31/505; C07D 487/04
[52] U.S. Cl. ...................................... 514/258; 544/263
[58] Field of Search ........................ 544/263; 514/258

[56] References Cited

U.S. PATENT DOCUMENTS

| | | | |
|---|---|---|---|
| 4,405,780 | 9/1983 | Wagner | 544/263 |
| 4,483,987 | 11/1984 | Wagner | 544/263 |
| 4,652,192 | 12/1985 | Wagner | 544/263 |

OTHER PUBLICATIONS

"Diuretics: Chemistry, Pharmacology and Clinical Applications", ed. J. B. Puschett, (Elsevier, New York, N.Y.) 1988.
"Drugs of the Future", vol. 10, No. 4, pp. 298–300 (1985).

Primary Examiner—Donald G. Daus
Attorney, Agent, or Firm—Frank P. Grassler; Paul D. Matukaitis

[57] ABSTRACT

1-(5-Amino-7-phenyl-[1,2,4] triazolo [1,5,c]pyrimidin-8-yl)-1, 2-ethan diol, a novel glycol of a triazolopyrimidine diuretic which is a metabolite and which exhibits fewer cardiotoxic side effects than the parent compound, but with no decrease in diuretic activity. The invention further provides for compositions incorporating the metabolite, and methods of its use as well as pharmaceutically acceptable salts thereof.

4 Claims, 1 Drawing Sheet a) Results are mean ± SEM, N=5.

b) Significantly different from saline control by unpaired t-test (p <0.05)

c) Significantly different from standard (HC, 0.6 mg/kg) by unpaired t-test (p <0.05).

DIOL METABOLITES OF 7-PHENYL-1,2,4-TRIAZOLO[2,3-C]PYRIMIDINES-5-AMINES

BACKGROUND OF THE INVENTION

The present invention provides a novel compound, novel compositions, methods of their use and methods of their manufacture, such compound being pharmacologically useful in inducing diuresis in a mammal and in the treatment of hypertension in a mammal. More specifically, the compound of the present invention is an orally active diol metabolite of a 7-phenyl-1 1,2,4-triazolo[2,3-c]pyrimidine-5-amine, which has diuretic activity comparable to that of its precursor, but with a lower incidence of side effects, especially cardiotoxic side effects.

Diuretics are drugs used to increase the volume of urine excreted by the kidneys. They are employed principally for the relief of edema and ascites. They are also especially useful in the treatment of hypertension. These conditions occur in diseases of the heart, kidneys and liver. Diuretics are most effective in the treatment of cardiac edema, particularly that associated with congestive heart failure. They are also used in the ascites of cirrhosis, nephrotic syndrome, diabetes insipidus, hypertension, edema of pregnancy, and to reduce cerebrospinal and intraocular fluid pressure. Some diuretics have highly specialized uses in glaucoma, hyperkalemia, bromide intoxication, anginal syndrome, epilepsy, migraines, and in premenstrual syndrome (i.e. conditions in which edema is not present or at least not definitely established).

The formation of urine from the blood, in simplest terms, consists of glomerular filtration and selective tubular reabsorption and secretion. As the glomerular filtrate passes through the tubules, substances essential to the blood and tissues - water, glucose, salts and amino acids - are reabsorbed. Other substances in the glomerular filtrate, such as urea, are not as readily absorbed by the tubules. Thus, it is thought that in the renal tubule, there is a specific mechanism for the transport of each ionic species, the capacities of which are quite different. For example, the capacity of the renal tubule to reabsorb sulfate ion is limited. By contrast, the tubular capacity for the reabsorption of phosphate is such that sufficient phosphate is reabsorbed to maintain the normal extracellular level and an excess is excreted. On the other hand, much larger amounts of bicarbonate ion and chloride ion can be reabsorbed.

Thiazide diuretics act mainly to block sodium and chloride reabsorption a the first (thick) portion of the distal tubule. They also have a mild anti-carbonic anhydrase effect. The resultant natriuresis is accompanied by increased excretion of potassium, bicarbonate, chloride and water.

The antihypertensive action of the thiazides is attributable to two factors: (a) depletion of sodium and subsequent reduction in plasma volume and (b) a decrease in peripheral resistance. The latter is thought t be due to the loss of sodium from the arteriolar wall or a direct action on the vascular bed. In addition, there is some inhibition of the pressor activity of norepinephrine. On the other hand, quantitative hypersensitivity to diuretics is frequently encountered. Other possible drawbacks are potassium deficiency, magnesium deficiency, pancreatitis, decreased glucose tolerance, increased uric acid levels and increased anticoagulant effects.

The compound of the general formula I:

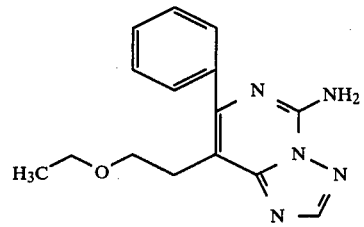

is disclosed in U.S. Pat. No. 4,405,780. This compound is a triazolopyrimidine diuretic which increases glomerular filtration rate and renal blood flow acutely in mammals. Chronic oral dosing showed significant increases in renal blood flow, glomerular filtration rate and sodium excretion.

The compound of the general formula II:

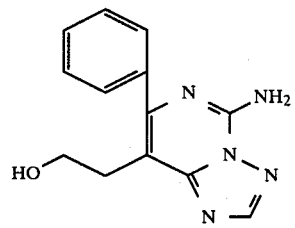

is disclosed in U.S. Pat. No. 4,483,987. Compound II is the o dealkylated metabolite of Compound I. It was subsequently discovered in this invention that compound II undergoes aliphatic hydroxylation in the rat. This was surprising and unexpected, since similar metabolism is not seen in man. The product of the subsequent hydroxylation step is represented by structural formula III:

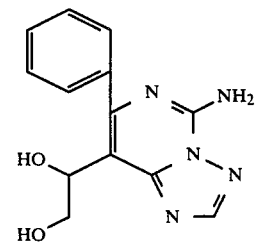

The compound of III provided three distinct surprising and unexpected advantages over either of the precursor compounds. Compound III is more water soluble, is more bioavailable, and shows no incidence of cardiotoxic side effects in rats.

SUMMARY OF THE INVENTION

The invention provides a compound of the formula

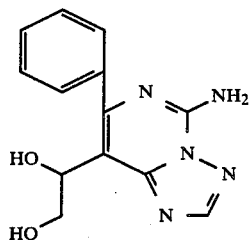

and the pharmaceutically acceptable salts thereof. This compound is useful in the treatment of hypertension, edema and ascites, as well as those pathological conditions that are ameliorated thereby.

The invention further provides dosage unit forms adapted for oral and parenteral administration.

DETAILED DESCRIPTION OF THE INVENTION

Figure 1:
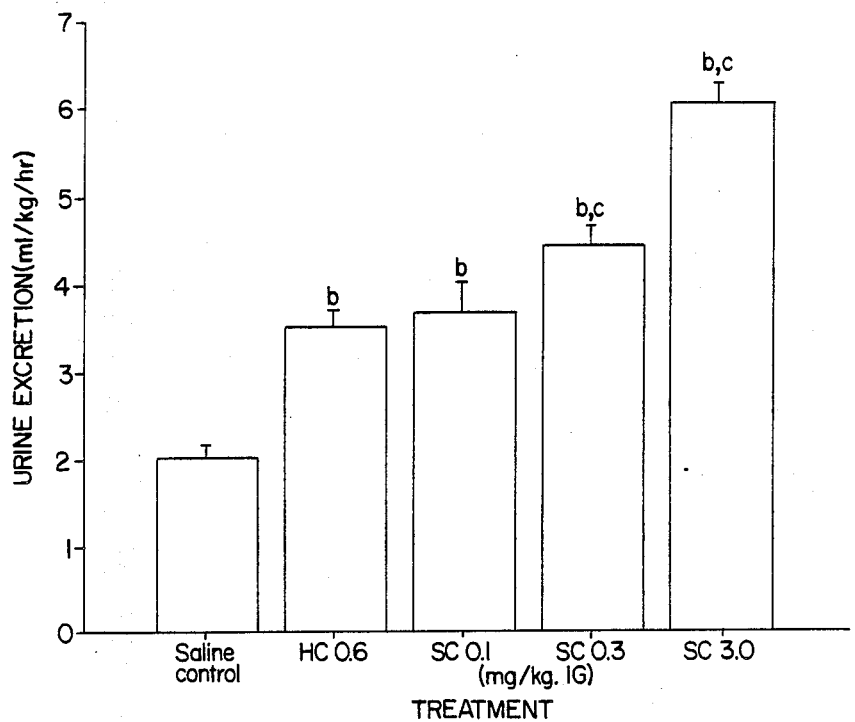

As used herein, the term "diuresis" shall mean an increased secretion of urine. The term "hypertension" shall mean a persistently high arterial blood pressure.

The term "pharmaceutically acceptable salts" refers to non-toxic salts of the compounds of this invention which are generally prepared by reacting the free base with a suitable organic or inorganic acid. Representative salts include the hydrochloride, hydroiodide, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, clavulanate and the like salts.

The most especially preferred compound representative of the invention is 1-(5-amino 7-phenyl-[1,2,4]triazolo-[1,5-c]pyrimidin-8-yl)-1,2-ethanediol, and the pharmaceutically acceptable salts thereof, and which is of the formula:

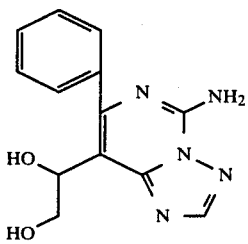

Compounds of the invention can be prepared readily according to the following reaction scheme or modifications thereof using readily available starting materials, reagents and conventional synthesis procedures. In these reactions, it is also possible to make use of variants which are in themselves known, but are not mentioned here in greater detail.

Scheme 1

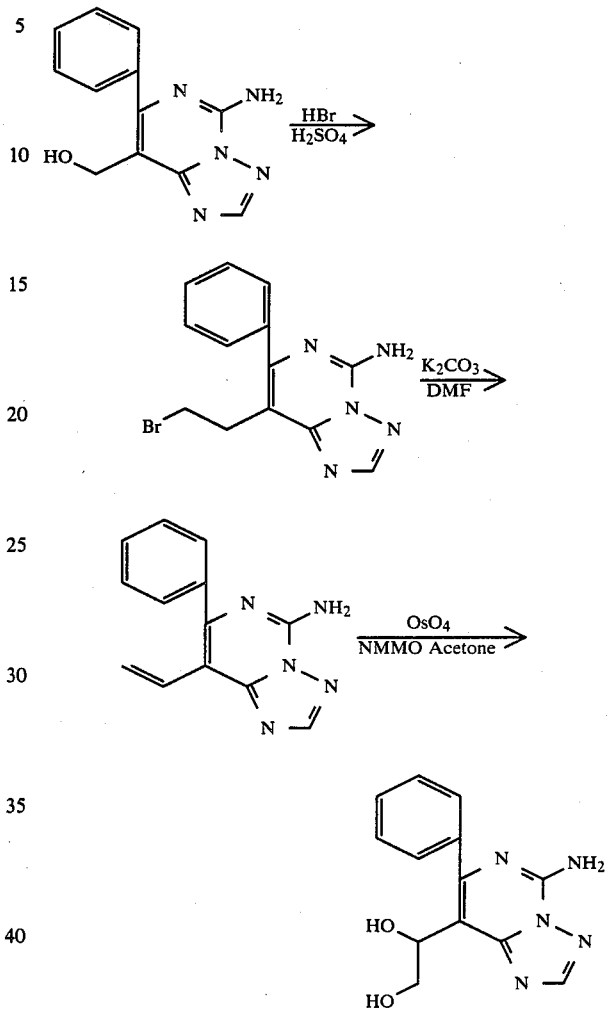

The compounds of the present invention can be administered in such oral dosage forms as tablets, capsules, pills, powders, granules, elixers, tinctures, suspensions, syrups and emulsions. Likewise, it may also be administered in intravenous, intraperitoneal, subcutaneous or intramuscular form, all using forms known to those of ordinary skill in the pharmaceutical arts. In general, the preferred form of administration is oral. An effective but non-toxic amount of the compound is employed in the treatment of ascites, edema, hypertension, congestive heart failure, or renal failure. The dosage regimen utilizing the compound of the present invention is selected in accordance with a variety of factors including the type, species, age, weight, sex and medical condition of the patient; the severity of the condition to be treated; the route of administration; the renal and hepatic function of the patient; and the particular compound or salt thereof employed. An ordinarily skilled veterinarian or physician can readily determine and prescribe the effective amount of the drug required to prevent, treat or arrest the progress of the condition.

Oral dosages of the compounds of the present invention, when used for the indicated effects, will range between about 0.1 mg/kg of body weight per day (mg/kg/day) to about 1,000 mg/kg/day and preferably 1.0–100 mg/kg/day. Advantageously, the compound of the present invention may be administered in a single daily dose or the total daily dosage may be administered in divided doses of 2, 3 or 4 times daily.

In the pharmaceutical compositions and methods of the present invention, the foregoing compound described in detail above will form the active ingredient that will typically be administered in an admixture with suitable pharmaceutical diluents, excipients or carriers (collectively referred to herein a "carrier" materials) suitably selected with respect to the intended form of administration, that is, oral tablets, capsules, elixirs, syrups and the like, and consistent with conventional pharmaceutical practices.

For instance, for oral administration in the form of tablets or capsules, the active drug component may be combined with an oral non toxic pharmaceutically acceptable inert carrier such as lactose, starch, sucrose, glucose, methylcellulose, magnesium stearate, dicalcium phosphate, calcium sulfate, mannitol, sorbitol and the like; for oral administration in liquid form, the active drug component may be combined with any oral nontoxic pharmaceutically acceptable inert carrier such as ethanol, glycerol, water, and the like. Moreover, when desired or necessary, suitable binders, lubricants, disintegrating agents and coloring agents can also be incorporated in the mixture. Suitable binders include starch, gelatin, natural sugars such as glucose or beta lactose, corn sweeteners, natural and synthetic gums such as acacia, tragacanth or sodium alginate, carboxymethylcellulose, polyethylene glycol and waxes. Lubricants for use in these dosage forms include magnesium stearate, sodium benzoate, sodium acetate, sodium stearate, sodium chloride, sodium oleate and the like. Disintegrators include, without limitation, starch, methylcellulose, agar, bentonite, xanthan gum and the like.

The compound of this invention exhibits diuretic activity useful in the treatment of ascites, hypertension, congestive heart failure, edema and renal failure. The test procedures employed to measure this activity of the compound of the present invention are described below.

EXAMPLE 1

Test animals are intact, normotensive male rats (Charles River Laboratories, Wilmington, Mass.) which are starved overnight with water ad lib. The animals are volume expanded on the day of the experiment with 25 ml/kg isotonic saline administered intragastrically. Experimental and standard compounds are administered as a suspension in an oral load. Hydrochlorothiazide is routinely used as the standard in this test at a dose of 0.2, 0.6 and 1.8 mg/kg. However, other standards may be used as deemed appropriate provided that potencies are clearly expressed in terms relative to that standard. Control animals are given isotonic saline alone.

Following saline and/or compound administration, rats are forced to void and are placed in pairs in clean, stainless steel metabolism cages for a five hour urine collection. At the end of five hours, rats are again forced to void residual bladder urine and are removed from the cage. Volume of urine is measured to the nearest 0.1 ml and expressed as urine excretion in ml/kg/hr. Results of administration of compound III are exhibited in FIG. I.

By virtue of the above described activity the compound of the invention is useful as a diuretic.

EXAMPLE 2

Cardiotoxicity study of compound III

Compound III was administered by gavage at 40 mg/kg, 80 mg/kg, 160 mg/kg and 320 mg/kg to female Charles River CD rats (10/dosage) once daily for three days. One additional group of rats received vehicle for three days to serve as controls. The purpose of this study was to determine whether myocardial lesions and associated changes found in rats treated with compounds I and II can also be induced by compound III. Additional groups of rats (3/dosage) were sacrificed two hours after dosing on day 1, blood collected, and samples analyzed to determine plasma concentrations of compound III.

None of the rats died. No lesions of the heart or adrenal gland were encountered in any of the rats by gross or histologic examination.

Mean plasma concentrations of compound III were 13.8, 19.8, 36.7 and 47.0 mcg/ml at 40, 80, 160 and 320 mg/kg respectively. These are well in excess of the concentrations that one might expect to see at cardiotoxic dosages of compounds I and II.

On the basis of this data, compound III does not appear to be cardiotoxic and, therefore not responsible for cardiotoxicity seen with compounds I and II. Ability to induce diuresis by administration of compound III may be expected to be useful in the treatment of congestive heart failure by inducing diuresis sufficient to reduce the afterload of the myocardium, as well as by treating the essential hypertension that in itself can be on of the causes of the decreased cardiac output that initiates the vicious cycle of the congestive heart failure syndrome.

The following non limiting examples further illustrate details for the preparation of the compound of the present invention. Those skilled in the art will readily understand that known variations of the conditions and processes of the following preparative procedures can be used to prepare these compounds. All temperatures are degrees Celsius unless otherwise noted. Unless otherwise noted, I.R. and N.M.R. spectra were consistent with the assigned structure.

EXAMPLE 3

8-(2-hydroxyethyl)-7-phenyl 1,2,4-triazolo[2,3-c]pyrimidine-5-amine

To a solution of 28 g (0.1 mmole) of 8-(2-ethoxyethyl)-7-phenyl-1,2,4-triazolo[2,3-c]pyrimidine-5-amine (which is prepared by methods described in U.S. Pat. No. 4,405,780, the entire disclosure of which is incorporated herein by reference) was added 200 mL of 1N boron trichloride and dichloromethane. The mixture was then stirred at room temperature overnight, after which 500 mL of water was added. After three hours, the resultant precipitate was collected by filtration. The agueous phase of the filter wa separated and neutralized with agueous sodium carbonate, giving a second precipitate. The combined solids were purified by column chromatography, giving the titled compound, m.p. 194°–195°.

Analysis calculated for $C_{13}H_{13}N_5O$: C 61.17; H, 5.13; n, 27.43. Found: C, 60.75; H, 5.06; N, 27.40.

EXAMPLE 4

8-(2-bromo)-7-phenyl-1,2,4-triazolo[2,3-c]pyrimidine-5-amine

A solution of the product of Example 3 is prepared in 50 mL ethanol, to which is added dropwise six drops of 48% HBr and two drops of $H_2SO_4$. The solution is heated on a steambath for one-half hour, then is allowed to stand at room temperature overnight In the morning heating is continued with another two drops of $H_2SO_4$ added for six and one-half hours. The residue is then taken up into an agueous $OH^-$ solution and extracted with ethylacetate to yield the product.

EXAMPLE 5

8-(1,2-ethyleneyl)-7-phenyl-1,2,4-triazolo[2,3-c]pyrimidine-5-amine 161 mg (0.49 mmole) of the product of Example 4 was added to 100 mg of 1,8-diazabicyclo (5.4.0)unda-7-ene (DBU) in 1 ml deimethylformamide (DMF). This solution was heated on a steam bath for ⅓ of an hour. The reaction mixture was cooled, water added, and a precipitate collected, as a crystalline solid giving the titled compound, m.p. 208°.

EXAMPLE 6

8-(1,2-dihydroxyethyl)-7-phenyl-1,2,4-triazolo[2,3-c]pyrimidine-5-amine 237 mg (1 mmole) of the olefin of Example 5 was added to 10 mL (2.22 mmole) of acetone, which was warmed sufficiently to dissolve the olefin, then cooled to room temperature, after which time 10 mg of osmiutetraoxide ($OsO_4$) in 300 mg of N-methylmorpholine oxide in t-butanol was added. The reaction mixture was stirred to dissolve the $OsO_4$. To the solution was then added 0.5 mL of an $OsO_4$/t-butanol solution (which was made from one gram $OsO_4$/50 mL t-butanol). The reaction mixture immediately turned deep green. After five minutes the color faded considerably. After fifteen minutes, the reaction mixture was a light yellow in color. The reaction mixture was then stirred for one and one-half hours. To the reaction mixture was then added 1 mL of a solution of one gram $Na_2S_2O_3$ and 5 mL $H_2O$ and the solution was stirred for several minutes until a dark residue separated from the solution. The solvent was decanted from the residue through a bed of Celite. The filtrate was separated and collected to yield 80 mg of product as white needles. The product was dried at 110° for one hour in vacuo.

Calculated for $C_{13}H_{13}N_5O_2$: C, 57.56; H, 4.83; N, 25.82. Found: C, 57.34; H, 4.89; N 25.71. M.P. 199°–200°.

While the invention has been described and illustrated with reference to certain prepared embodiments thereof, those skilled in the art will appreciate that various changes, modifications and substitutions can be made therein without departing from the spirit and scope of the invention. For example, effective dosages other than the preferred range as set forth herein above may be applicable as a consequence of variations in the responsiveness of the mammal being treated for severity of hypertension, congestive heart failure or renal failure; dosage related adverse effects, if any; and analogous considerations. Likewise, the specific pharmacological responses observed may vary according to and depending upon the particular active compound selected or whether there are at present certain pharmaceutical carriers, as well as the type of formulation and mode of administration employed, and such expected variations or differences in the results are contemplated in accordance with the objects and practices of the present invention. It is intended therefore that the invention be limited only by the scope of the claims which follow, and that such claims be interpreted as broadly as is reasonable.

What is claimed is:

1. A compound of the structure

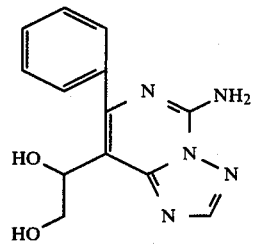

and the pharmaceutically acceptable salts thereof.

2. A pharmaceutical composition comprising a pharmaceutically acceptable non toxic carrier and the compound as claimed in claim 1, namely 1-(5-amino-7-phenyl-[1,2,4]triazolo[1,5-c]pyrimidin-8-yl)-1,2-ethanediol.

3. A method of inducing diuresis in a mammal, comprising administering to said mammal a pharmacologically effective amount of the compound as claimed in claim 1.

4. A method of treating hypertension in a mammal, comprising administering to said mammal a pharmacologically effective amount of the compound as claimed in claim 1.

* * * * *

UNITED STATES PATENT AND TRADEMARK OFFICE
CERTIFICATE OF CORRECTION

PATENT NO. : 4,866,063
DATED : Sep. 12, 1989
INVENTOR(S) : Burton et al.

It is certified that error appears in the above-identified patent and that said Letters Patent is hereby corrected as shown below:

Column 1, line 50, reading "an" should read -- any.

Column 3, line 42, reading "-amino  7-" should read -- -amino-7- --.

Column 4, Scheme 1, the first structure, reading

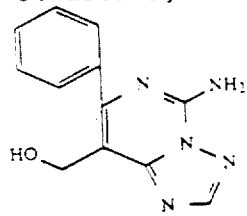

should read

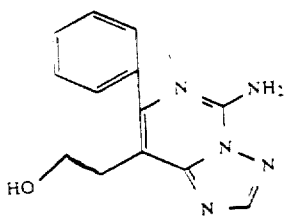

UNITED STATES PATENT AND TRADEMARK OFFICE
CERTIFICATE OF CORRECTION

PATENT NO. : 4,866,063

DATED : Sep. 12, 1989

INVENTOR(S) : Burton et al.

It is certified that error appears in the above-identified patent and that said Letters Patent is hereby corrected as shown below:

Column 6, lines 50-51, reading "-phenyl 1,2,4-" should read -- phenyl-1,2,4- --

Signed and Sealed this

Twenty-eighth Day of May, 1991

Attest:

HARRY F. MANBECK, JR.

Attesting Officer

Commissioner of Patents and Trademarks